United States Patent
Yencho et al.

(10) Patent No.: US 6,776,785 B1
(45) Date of Patent: Aug. 17, 2004

(54) IMPLANTABLE SUPERELASTIC ANASTOMOSIS DEVICE

(75) Inventors: Stephen Yencho, Menlo Park, CA (US); Jaime Vargas, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 211 days.

(21) Appl. No.: 09/687,216

(22) Filed: Oct. 12, 2000

(51) Int. Cl.$^7$ .............................................. A61B 17/08

(52) U.S. Cl. ...................................................... 606/153

(58) Field of Search ................................. 606/153, 151, 606/154, 155, 156, 157, 158

(56) References Cited

U.S. PATENT DOCUMENTS

| | | | |
|---|---|---|---|
| 3,155,095 A | * | 11/1964 | Brown |
| 3,254,650 A | | 6/1966 | Collito |
| 3,519,187 A | | 7/1970 | Kapitanov et al. |
| 3,774,615 A | | 11/1973 | Lim et al. |
| 4,214,587 A | * | 7/1980 | Sakura, Jr. |
| 4,350,160 A | | 9/1982 | Kolesov et al. |
| 4,352,358 A | | 10/1982 | Angelchik |
| 4,366,819 A | | 1/1983 | Kaster |
| 4,368,736 A | | 1/1983 | Kaster |
| 4,503,568 A | | 3/1985 | Madras |
| 4,523,592 A | | 6/1985 | Daniel |
| 4,553,542 A | | 11/1985 | Schenck et al. |
| 4,589,416 A | | 5/1986 | Green |
| 4,593,693 A | | 6/1986 | Schenck |
| 4,603,693 A | | 8/1986 | Conta et al. |
| 4,607,637 A | | 8/1986 | Berggren et al. |
| 4,624,255 A | | 11/1986 | Schenck et al. |
| 4,624,257 A | | 11/1986 | Berggren et al. |
| 4,657,019 A | | 4/1987 | Walsh et al. |
| 4,665,906 A | | 5/1987 | Jervis |
| 4,747,407 A | | 5/1988 | Liu et al. |
| 4,752,024 A | | 6/1988 | Green et al. |
| 4,883,453 A | | 11/1989 | Berry et al. |
| 4,892,098 A | | 1/1990 | Sauer |
| 4,907,591 A | | 3/1990 | Vasconcellos et al. |
| 4,917,087 A | | 4/1990 | Walsh et al. |
| 4,917,090 A | | 4/1990 | Berggren et al. |
| 4,917,091 A | | 4/1990 | Berggren et al. |
| 4,930,674 A | | 6/1990 | Barak |
| 5,005,749 A | | 4/1991 | Aranyi |
| 5,062,842 A | | 11/1991 | Tiffany |
| 5,104,025 A | | 4/1992 | Main et al. |
| 5,119,983 A | | 6/1992 | Green et al. |
| 5,129,913 A | | 7/1992 | Ruppert |
| 5,156,613 A | | 10/1992 | Sawyer |
| 5,171,262 A | | 12/1992 | MacGregor |
| 5,187,796 A | | 2/1993 | Wang et al. |
| 5,193,731 A | | 3/1993 | Aranyi |
| 5,205,459 A | | 4/1993 | Brinkerhoff et al. |
| 5,217,474 A | | 6/1993 | Zacca et al. |
| 5,221,281 A | | 6/1993 | Klicek |
| 5,222,963 A | | 6/1993 | Brinkerhoff et al. |
| 5,234,447 A | * | 8/1993 | Kaster et al. |
| 5,250,058 A | | 10/1993 | Miller et al. |

(List continued on next page.)

FOREIGN PATENT DOCUMENTS

| | | |
|---|---|---|
| DE | 29713335.7 | 11/1997 |
| EP | 0517252 | 12/1992 |
| EP | 0 701 800 | 3/1996 |

(List continued on next page.)

*Primary Examiner*—Ismael Izaguirre
(74) *Attorney, Agent, or Firm*—Brian A. Schar; Cindy A. Lynch

(57) ABSTRACT

A one piece anastomosis device is disclosed which is formed of a superelastic or pseudoelastic material which self deforms or self deploys from an insertion configuration to a tissue holding configuration. The device in a deployed state preferably includes an inner tissue penetrating flange which penetrate and retains an everted graft vessel and an outer flange. The self deploying anastomosis device does not rely on a temperature transformation to achieve deployment.

24 Claims, 10 Drawing Sheets

U.S. PATENT DOCUMENTS

| | | |
|---|---|---|
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,443,497 A | 8/1995 | Venbrux |
| 5,447,514 A | 9/1995 | Gerry et al. |
| 5,454,825 A | 10/1995 | Van Leeuwen et al. |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | LeMole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,976,159 A | 11/1999 | Bolduc et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinski et al. |
| 6,036,703 A | 3/2000 | Evans et al. |
| 6,036,704 A | 3/2000 | Yoon |
| 6,036,705 A | 3/2000 | Nash et al. |
| 6,050,472 A | 4/2000 | Shibata |
| 6,053,390 A | 4/2000 | Green et al. |
| 6,056,762 A | 5/2000 | Nash et al. |
| 6,066,144 A | 5/2000 | Wolf et al. |
| 6,066,148 A | 5/2000 | Rygaard |
| 6,068,637 A | 5/2000 | Popov et al. |
| 6,074,416 A | 6/2000 | Berg et al. |
| 6,080,167 A | 6/2000 | Lyell |
| 6,080,173 A | 6/2000 | Williamson, IV et al. |
| 6,083,234 A | 7/2000 | Nicholas et al. |
| 6,110,188 A | 8/2000 | Narciso, Jr. |
| 6,113,612 A | 9/2000 | Swanson et al. |
| 6,117,148 A | 9/2000 | Ravo et al. |
| 6,120,432 A | 9/2000 | Sullivan et al. |
| 6,146,393 A | 11/2000 | Wakabayashi |
| 6,149,681 A | 11/2000 | Houser et al. |
| 6,152,937 A | 11/2000 | Peterson et al. |
| 6,152,945 A | 11/2000 | Bachinski et al. |
| 6,165,185 A | 12/2000 | Shennib et al. |
| 6,167,889 B1 | 1/2001 | Benetti |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,186,942 B1 | 2/2001 | Sullivan et al. |
| 6,187,019 B1 | 2/2001 | Stefanchik et al. |
| 6,187,020 B1 | 2/2001 | Zegdi et al. |
| 6,190,396 B1 | 2/2001 | Whitin et al. |
| 6,190,397 B1 | 2/2001 | Spence et al. |
| 6,190,590 B1 | 2/2001 | Randall et al. |
| 6,193,129 B1 | 2/2001 | Bittner et al. |
| 6,193,734 B1 * | 2/2001 | Bolduc et al. |
| 6,206,912 B1 | 3/2001 | Goldsteen et al. |
| 6,206,913 B1 | 3/2001 | Yencho et al. |
| 6,428,550 B1 * | 8/2002 | Vargas et al. ............... 606/153 |
| 6,440,163 B1 * | 8/2002 | Swanson et al. ........... 623/1.23 |
| 6,511,491 B2 * | 1/2003 | Grudem et al. ............. 606/153 |
| 6,599,303 B1 | 7/2003 | Peterson et al. |
| 6,602,263 B1 | 8/2003 | Swanson et al. |
| 6,605,098 B2 * | 8/2003 | Nobis et al. ................ 606/153 |

FOREIGN PATENT DOCUMENTS

| | | |
|---|---|---|
| EP | 0 885 595 | 12/1998 |
| EP | 0 938 870 | 9/1999 |

| | | | | | |
|---|---|---|---|---|---|
| EP | 0 820 724 | 1/2000 | WO | 99/65409 | 12/1999 |
| EP | 0 820 725 | 1/2000 | WO | 00/09040 | 2/2000 |
| EP | 0 913 125 | 7/2000 | WO | 00/10486 | 3/2000 |
| EP | 0 990 420 | 12/2000 | WO | 00/12013 | 3/2000 |
| WO | 92/08513 | 5/1992 | WO | 00/15144 | 3/2000 |
| WO | 96/25886 | 8/1996 | WO | 00/15146 | 3/2000 |
| WO | 97/25002 | 7/1997 | WO | 00/15147 | 3/2000 |
| WO | 97/27898 | 8/1997 | WO | 00/15148 | 3/2000 |
| WO | 97/31575 | 9/1997 | WO | 00/15149 | 3/2000 |
| WO | 97/47261 | 12/1997 | WO | 00/27310 | 5/2000 |
| WO | 98/07399 | 2/1998 | WO | 00/27311 | 5/2000 |
| WO | 98/19608 | 5/1998 | WO | 00/27312 | 5/2000 |
| WO | 98/19618 | 5/1998 | WO | 00/27313 | 5/2000 |
| WO | 98/19625 | 5/1998 | WO | 00/33745 | 6/2000 |
| WO | 98/19629 | 5/1998 | WO | 00/41633 | 7/2000 |
| WO | 98/19630 | 5/1998 | WO | 00/53104 | 9/2000 |
| WO | 98/19631 | 5/1998 | WO | 00/56223 | 9/2000 |
| WO | 98/19632 | 5/1998 | WO | 00/56226 | 9/2000 |
| WO | 98/19634 | 5/1998 | WO | 00/56227 | 9/2000 |
| WO | 98/19636 | 5/1998 | WO | 00/56228 | 9/2000 |
| WO | 98/30153 | 7/1998 | WO | 00/59380 | 10/2000 |
| WO | 98/37814 | 9/1998 | WO | 00/66007 | 11/2000 |
| WO | 98/42262 | 10/1998 | WO | 00/66009 | 11/2000 |
| WO | 98/47430 | 10/1998 | WO | 00/69343 | 11/2000 |
| WO | 98/55027 | 12/1998 | WO | 00/69346 | 11/2000 |
| WO | 99/08603 | 2/1999 | WO | 00/69349 | 11/2000 |
| WO | 99/17665 | 4/1999 | WO | 00/69364 | 11/2000 |
| WO | 99/18887 | 4/1999 | WO | 00/72764 | 12/2000 |
| WO | 99/21491 | 5/1999 | WO | 00/74579 | 12/2000 |
| WO | 99/37218 | 7/1999 | WO | 00/76405 | 12/2000 |
| WO | 99/38441 | 8/1999 | WO | 01/08601 | 2/2001 |
| WO | 99/38454 | 8/1999 | WO | 01/12074 | 2/2001 |
| WO | 99/40851 | 8/1999 | WO | 01/15607 | 3/2001 |
| WO | 99/40868 | 8/1999 | WO | 01/17440 | 3/2001 |
| WO | 99/45848 | 9/1999 | WO | 01/19257 | 3/2001 |
| WO | 99/52481 | 10/1999 | WO | 01/19259 | 3/2001 |
| WO | 99/62406 | 12/1999 | WO | 01/19284 | 3/2001 |
| WO | 99/62409 | 12/1999 | WO | 01/34037 | 5/2001 |
| WO | 99/62415 | 12/1999 | | | |
| WO | 99/63910 | 12/1999 | | | |

* cited by examiner

IMPLANTABLE SUPERELASTIC ANASTOMOSIS DEVICE

BACKGROUND OF THE INVENTION

1. Field of the Invention

The invention relates to an implantable medical device such as an anastomosis device and a deployment system for implanting the device. In a preferred embodiment, the device can be used for forming a sutureless connection between a bypass graft and a blood vessel.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

Accordingly, it would be desirable to provide a sutureless vascular anastomosis device which easily connects a graft to a target vessel. It would also be desirable to provide a sutureless anastomosis device which is formed of one piece and is secured to the target vessel in a single step.

SUMMARY OF THE INVENTION

A superelastic or pseudoelastic one piece anastomosis device according to the present invention connects a graft vessel to a target vessel. The anastomosis device deforms from an insertion configuration to a tissue holding configuration due to the superelastic or pseudoelastic properties of the material.

In accordance with one aspect of the present invention, a one piece anastomosis device for connecting a graft vessel to a target vessel includes a device body formed of a superelastic or pseudoelastic material. The device body has an insertion configuration and a tissue holding configuration in which the body has an inner flange and an outer flange. At least one of the inner and outer flanges is radially constrained in the insertion configuration for insertion into the target vessel. When the device body is released it self deforms to the tissue holding configuration.

In accordance with another aspect of the present invention, a tube deployed anastomosis system for connecting a graft vessel to a target vessel includes a deployment tube and an anastomosis device formed of a superelastic or pseudoelastic material. The device has an insertion configuration and a tissue holding configuration in which the device has an inner flange and an outer flange. The inner and outer flanges are radially constrained in the deployment tube in the insertion configuration for insertion into the target vessel and when released from the deployment tube, the device self deforms to the tissue holding configuration.

In accordance with another further aspect of the present invention, a method of deploying an anastomosis system for connecting a graft vessel to a target vessel includes the steps of: connecting a graft vessel to a one piece device formed of a superelastic or pseudoelastic material; poking a portion of the one piece device through the graft vessel; and deploying the one piece device by self deformation to a tissue holding configuration in which the device has an inner flange and an outer flange and traps the target vessel tissue between the inner flange and the outer flange.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

The present invention relates to a superelastic or pseudoelastic anastomosis device and method for connecting a graft vessel to a target vessel without the use of conventional sutures. The quick and easy deployment of the anastomosis system according to the present invention greatly increases the speed with which anastomosis can be performed over the known sutured anastomosis methods. The anastomosis devices according to the present invention are particularly designed for use in connecting graft vessels to target vessel in a variety of anastomosis procedures, including coronary artery bypass grafting. In such procedures, a large vessel anastomotic device is used to connect a graft vessel to large diameter target vessels such as the aorta or it's major side branches and a small vessel anastomotic device is used for connecting a graft vessel to a target vessel having a small diameter such as a coronary artery.

Suturing a graft vessel to a target vessel with conventional procedures is difficult and time consuming, particularly in minimally invasive procedures where space may be limited and in procedures in which it may be desired to perform an anastomosis without stoppage of blood flow through the target vessel. The superelastic or pseudoelastic anastomosis device and method of the present invention allow anastomosis to be performed efficiently and effectively in tight spaces. The anastomosis may also be performed with or without stoppage of blood flow in a target vessel and with or without the use of cardiopulmonary bypass.

Figure 1:
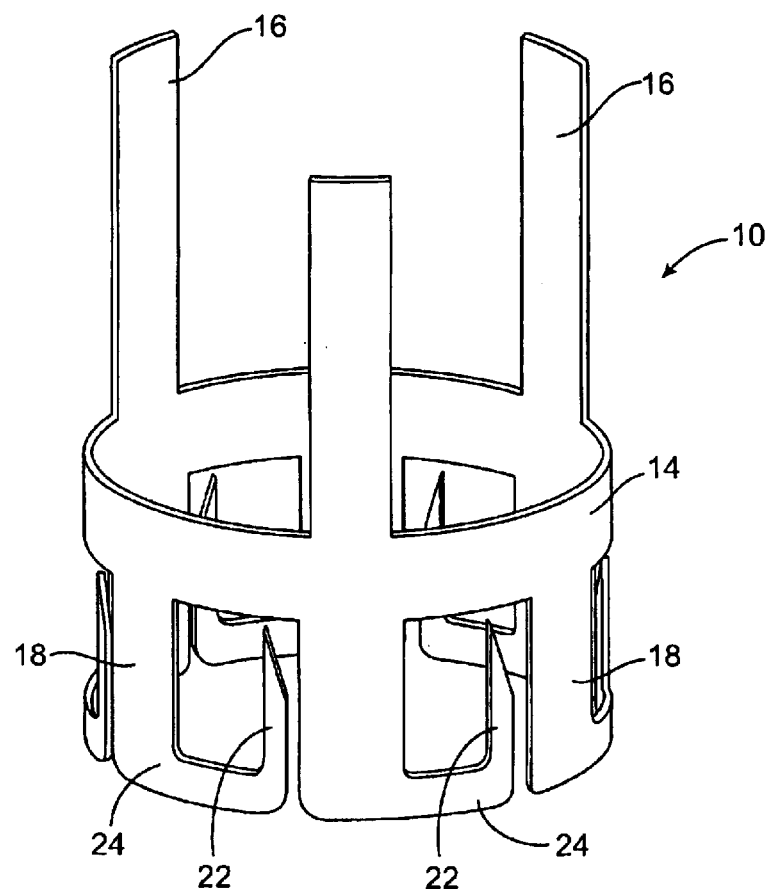
FIG. 1 is a perspective view of a first embodiment of an anastomosis device in a constrained configuration prior to use.
Figure 2:
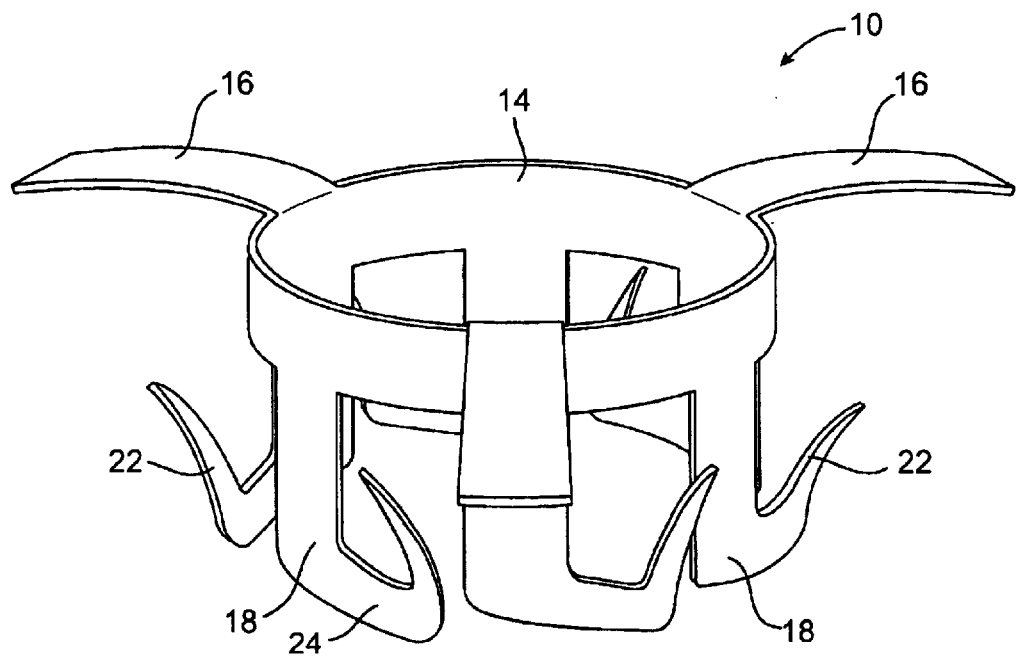
FIG. 2 is a perspective view of the anastomosis device of FIG. 1 in a deployed configuration.

FIG. 1 illustrates an anastomosis device 10 according to a first embodiment of the present invention in a constrained insertion configuration in which the anastomosis device would be inserted into a target blood vessel. FIG. 2 illustrates the anastomosis device 10 of FIG. 1 in an expanded deployed configuration which holds a graft vessel to a target vessel. The superelastic or the pseudoelastic anastomosis device in FIG. 1 includes a substantially cylindrical body 14, a plurality of legs 16 extending from a first side of the body, and a plurality of hooks 18 extended from a second side of the body. In the insertion configuration illustrated in FIG. 1, the body 14, the legs 16, and the hooks 18, are substantially aligned in a constrained substantially cylindrical shape. The anastomosis device 10 may be held in the constrained substantially cylindrical shape by a deployment tool, such as a substantially cylindrical deployment tube. When the deployment tool is removed from the device 10, the device returns to a preset expanded shape illustrated in FIG. 2 due to the superelastic or pseudoelastic properties of the material.

The anastomosis device 10 is made of a pseudoelastic or superelastic alloy, such as Nitinol or other pseudoelastic or superelastic material. The superelastic or pseudoelastic device 10 will self deform through superelastic or pseudoelastic behavior from the constrained insertion configuration illustrated in FIG. 1 to the expanded configuration illustrated in FIG. 2 when the constraining device or deployment tool is removed. The anastomosis device 10 formed of the superelastic or pseudoelastic material is formed in the final shape illustrated in FIG. 2 and is then isothermally deformed by constraining in a tube or other deployment tool in the substantially cylindrical shape illustrated in FIG. 1. The need for temperature control is avoided since the anastomosis device 10 reforms the deployed shape of FIG. 2 spontaneously when removed from the constraining tube. This allows the accurate placement of the anastomosis device 10 spontaneously and nearly instantaneously upon deployment of the device. The need for a mechanical deployment device to mechanically deform the anastomosis device from the insertion configuration to the deployed configuration is also avoided.

The anastomosis devices of the present invention may be made of any known superelastic or pseudoelastic material. U.S. Pat. No. 5,597,378 provides a discussion of superelastic and pseudoelastic materials and is incorporated herein by reference in its entirety.

The deployed anastomosis device 10 as shown in FIG. 2 includes an inner flange formed by outwardly extruding ends 22 of the J-shaped hooks 18. The deployed device 10 also includes an outer flange formed by the legs 16 extending outward from the body 14.

Figure 3:
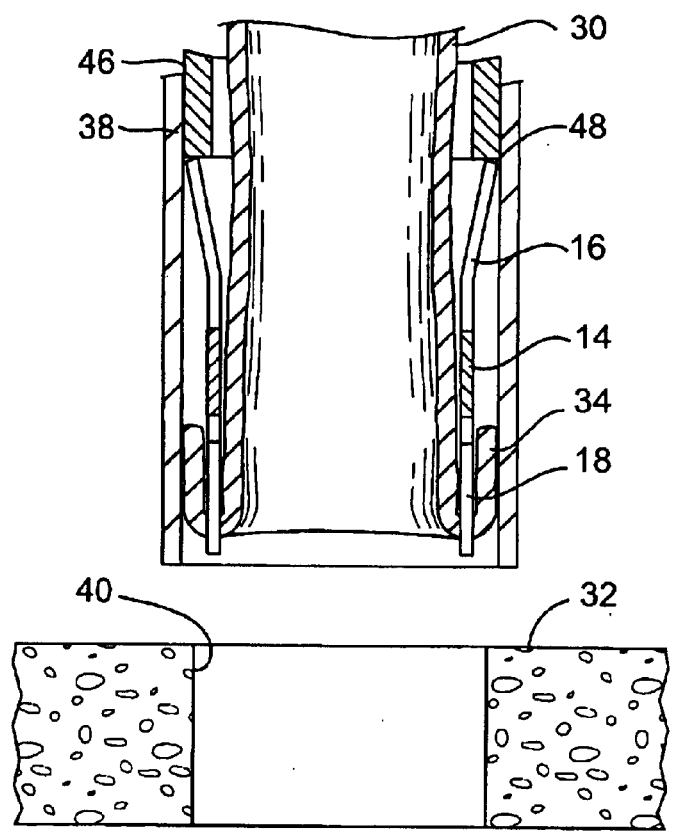
FIG. 3 is a side cross sectional view of the anastomosis device of FIG. 1 with a graft vessel everted around the device and the device constrained by a tube prior to deployment.

In use, a graft vessel 30, shown in FIG. 3, is threaded through a center of the anastomosis device 10. An end 34 of the graft vessel 30 is everted around the hooks 18 and the hook ends 22 penetrate into or through the everted end 34 of the graft vessel retaining the graft vessel in place on the anastomosis device 10.

As illustrated in FIG. 3, the anastomosis device 10 with the everted graft vessel 30 is positioned within a deployment tube 38 for delivery of the anastomosis device and graft vessel to an opening 40 in a target vessel 32. In the radially constrained insertion configuration, the leading edge or hook end of the anastomosis device may be substantially cylindrical or slightly conical for ease of insertion.

One embodiment of a method for deploying the anastomosis device 10 of the present invention will be described with reference to FIGS. 3–6. As shown in FIG. 3, the graft vessel 30 is prepared by everting an end 34 of the graft vessel around the hooks 18 of the anastomosis device 10. The hook ends 22 penetrate the graft vessel tissue to maintain the everted configuration of the graft vessel. The hooks 18 and the legs 16 of the anastomosis device 10 are radially constrained by inserting the anastomosis device 10 and everted end of the graft vessel 30 into a deployment tool 38 in the shape of a tube. When positioned inside the deployment tool 38, the anastomosis device 10 is in a generally cylindrical configuration for insertion into the target vessel 32.

Figure 4:
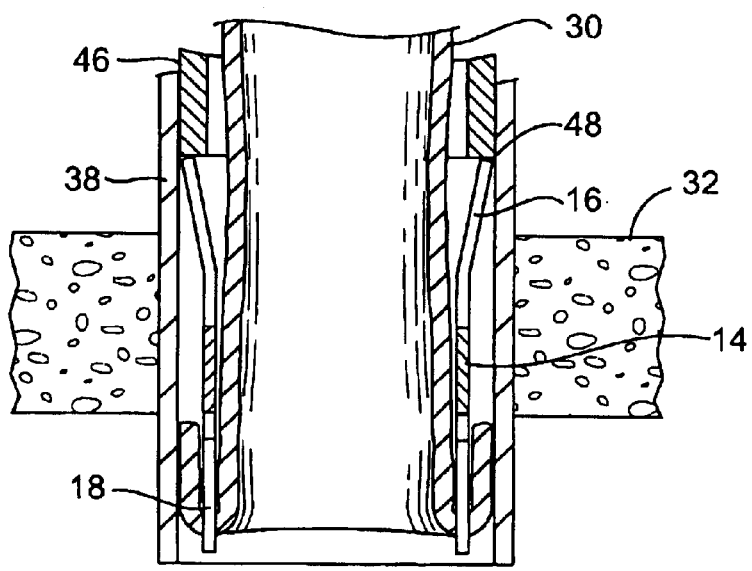
FIG. 4 a side cross sectional view of the system of FIG. 3 being inserted into a target vessel.

As shown in FIG. 4, the deployment tool 38 is used to insert the anastomosis device 10 and the graft vessel 30 into the target vessel 32 until the hook ends 22 have passed through the opening 40 and are positioned within an interior of the blood vessel. As shown in FIGS. 3 and 4, a retainer tube 36 is positioned around the graft vessel 30 and inside the deployment tool 38 for holding and extruding the anastomosis device 10. A distal end 48 of the retainer tube 46 is positioned adjacent to a proximal end of the anastomosis device 10. The distal end 48 of the retainer tube 46 may be attached to or abut the anastomosis device 10 to hold the anastomosis device in place inside the deployment tube 38 during the insertion step of FIG. 4.

Figure 5:
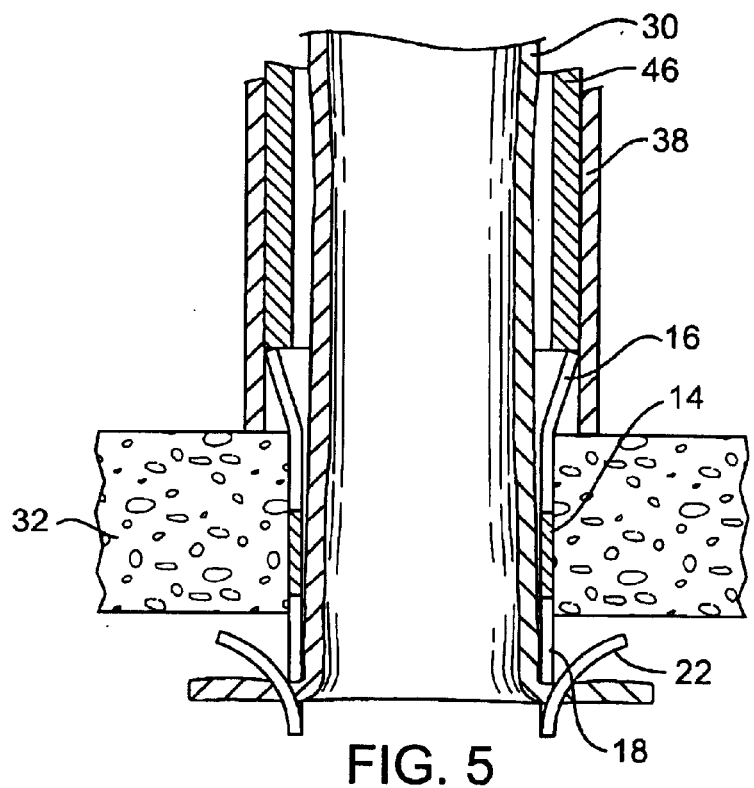
FIG. 5 is a side cross sectional view of the system of FIG. 3 after release of an inner flange.

As shown in FIG. 5, the anastomosis device 10 is held in place by the retainer tube 46 while the deployment tube 38 is withdrawn or retracted to release the radial constraining force from the hooks 18. Upon removal of the deployment tube 38 from the hooks 18, the hook ends 22 and hook base portion 24 spontaneously spring outward due to the superelasticity or pseudoelasticity of the material.

Figure 6:
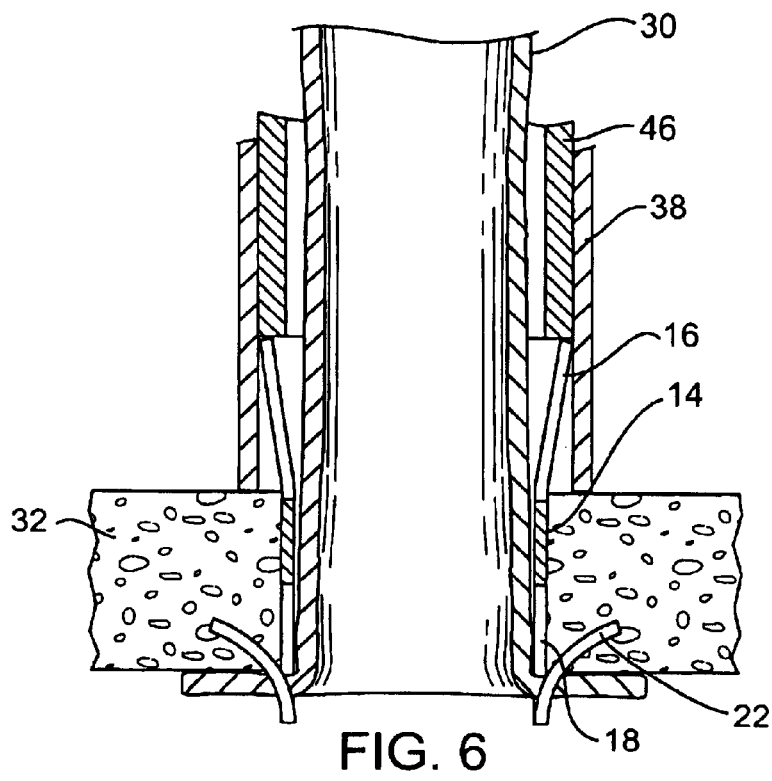
FIG. 6 is a side cross sectional view of the system of FIG. 3 with the inner flange imbedded in an inner wall of the target vessel wall.
Figure 7:
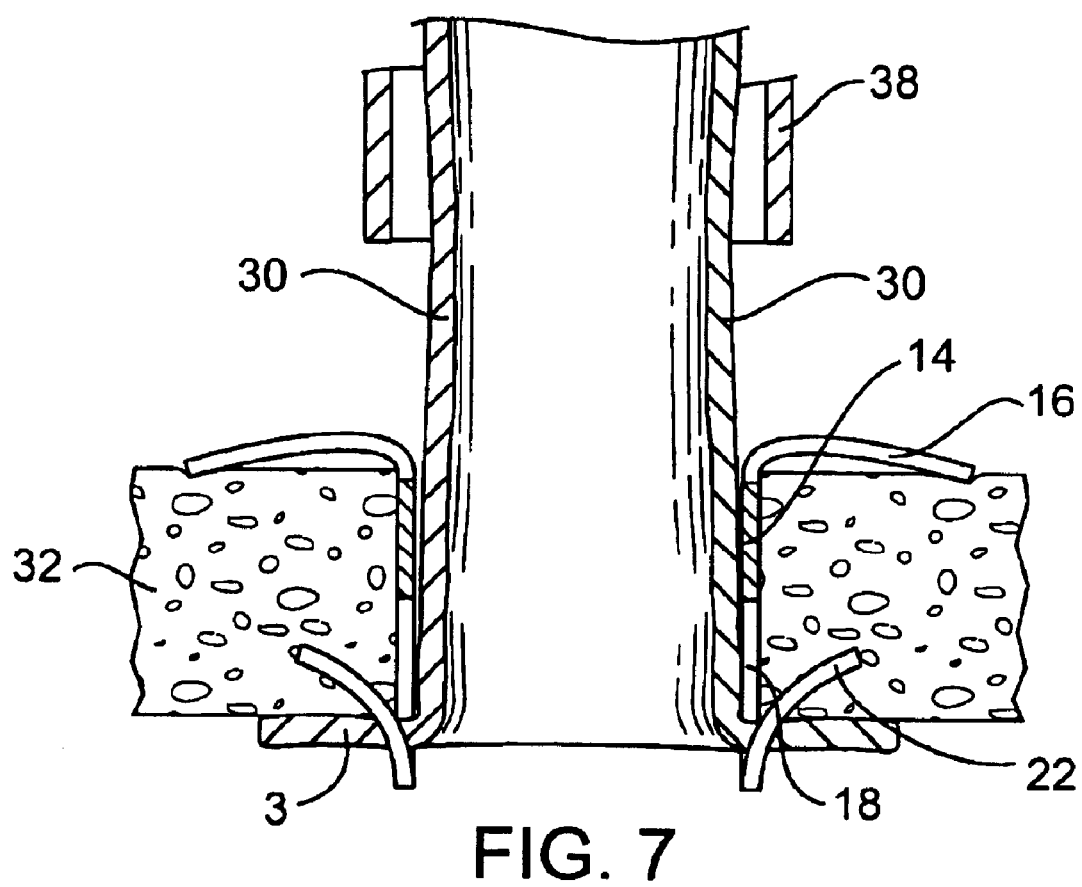
FIG. 7 is a side cross sectional view of the system of FIG. 3 after release of the outer flange showing the deployment tube being removed.

As shown in FIG. 6, after the release of the hooks 18 the anastomosis device 10 is withdrawn by the deployment tool 38 against the interior wall of the target vessel 32 causing the hook ends 22 to be compressed against or penetrate into the tissue of the interior wall of the target vessel. The deployment tube 38 is then completely withdrawn as shown in FIG. 7 allowing the legs 16 to spontaneously spring outward to trap the wall of the target vessel 32 between the hooks 18 which form an inner flange and the legs 16 which form an outer flange for the deployed anastomosis device 10.

Figure 8:
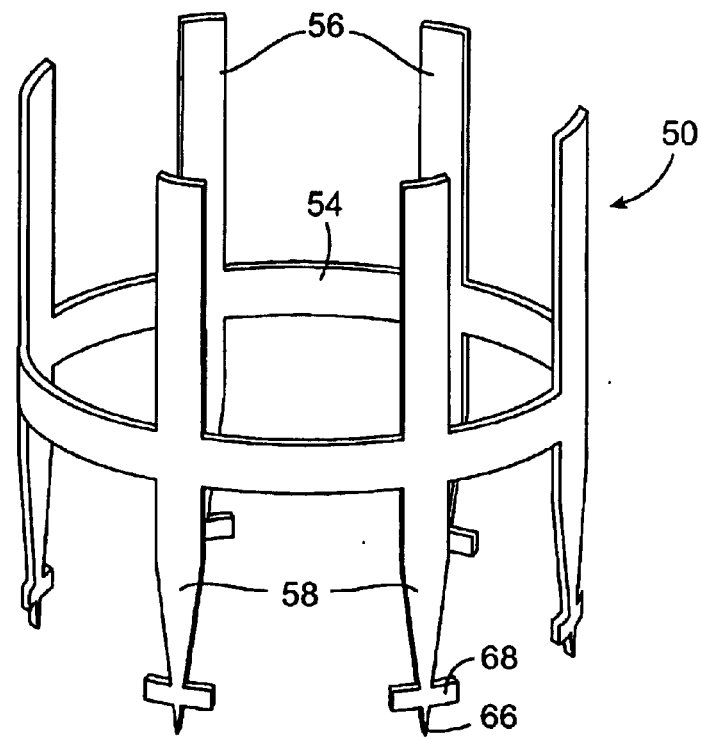
FIG. 8 is a perspective view of an alternative embodiment of an anastomosis device in a constrained configuration prior to use.
Figure 9:
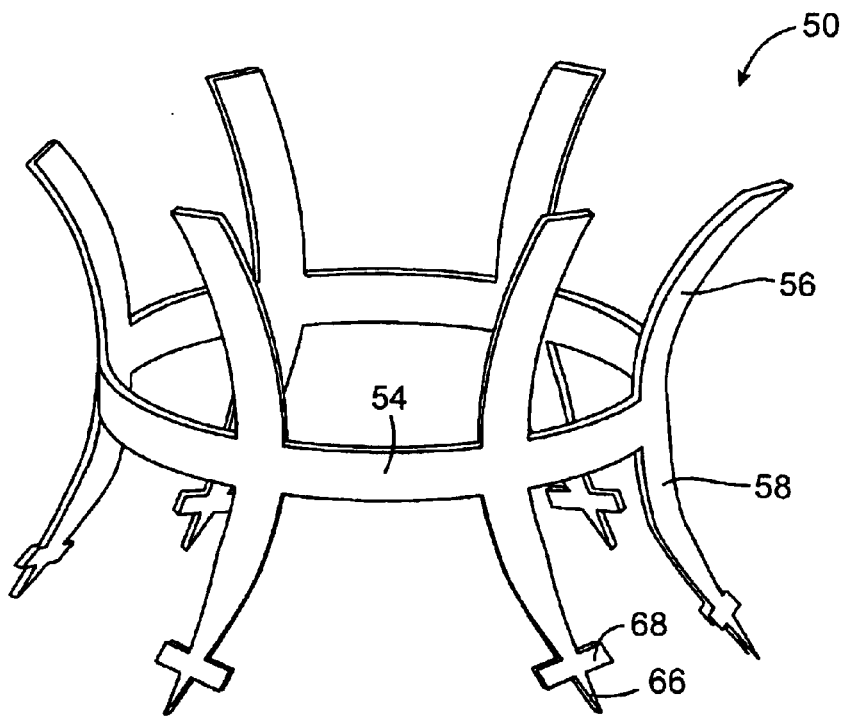
FIG. 9 is a perspective view of the anastomosis device of FIG. 8 in a deployed configuration.
Figure 10:
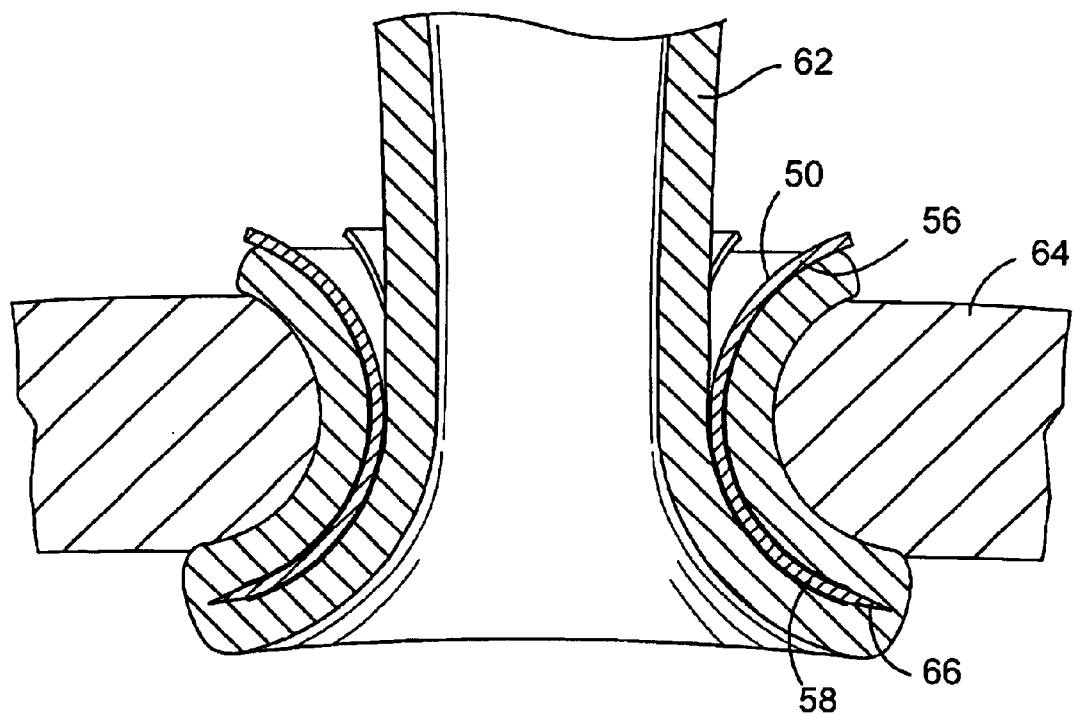
FIG. 10 is side cross sectional view of the anastomosis device of FIG. 8 after deployment shown connecting a graft and a target vessel.

FIGS. 8–10 illustrate an alternative embodiment of an anastomosis device 50 having a central body portion 54. A first set of legs 56 extend from one end of the body 54 and a second set of pointed legs 58 extend from the second side of the body. In a constrained configuration illustrated in FIG. 8, the anastomosis device 50 is substantially tubular for insertion into a target vessel. In an expanded deployed configuration, illustrated in FIGS. 9 and 10, the anastomosis device 50 is substantially C-shaped in cross section with the legs 56 forming an outer flange and the pointed legs 58 forming an inner flange of the anastomosis device 50.

The embodiment shown in FIGS. 8–10 may be deployed in a manner similar to that of the anastomosis device described above with respect to FIGS. 1–7. As shown in FIG. 10, the graft vessel 62 is everted around the anastomosis device 50. The anastomosis device 50 and graft vessel 62 are then inserted into an opening in the target vessel 64 in a constrained configuration. A constraining device such as the deployment tool 38 is then removed from the anastomosis device 50 and graft vessel 62 allowing the legs 56 and 58 to spontaneously spring outward by the superelastic or pseudoelastic properties of the material to form inner and outer flanges which trap the tissue of the target vessel 64 between the inner and outer flanges.

According to one preferred embodiment of the anastomosis device 50 the pointed legs 58 each include a pointed tissue penetrating end 66 and a rectangular stop member 68 for limiting the tissue penetration of the penetrating end. As shown in FIG. 10, the tissue penetrating end 66 of the pointed legs 58 penetrates into or through the graft vessel 62 to ensure the graft vessel is retained on the anastomosis device 50 during and after deployment.

In the deployed configuration illustrated in FIG. 10, the intima of the graft vessel 62 abuts an intima of the target vessel 64. Thus, the expansion of the inner flange of the anastomosis device 50 forms a vein gasket to seal the graft and target vessels together.

Figure 11:
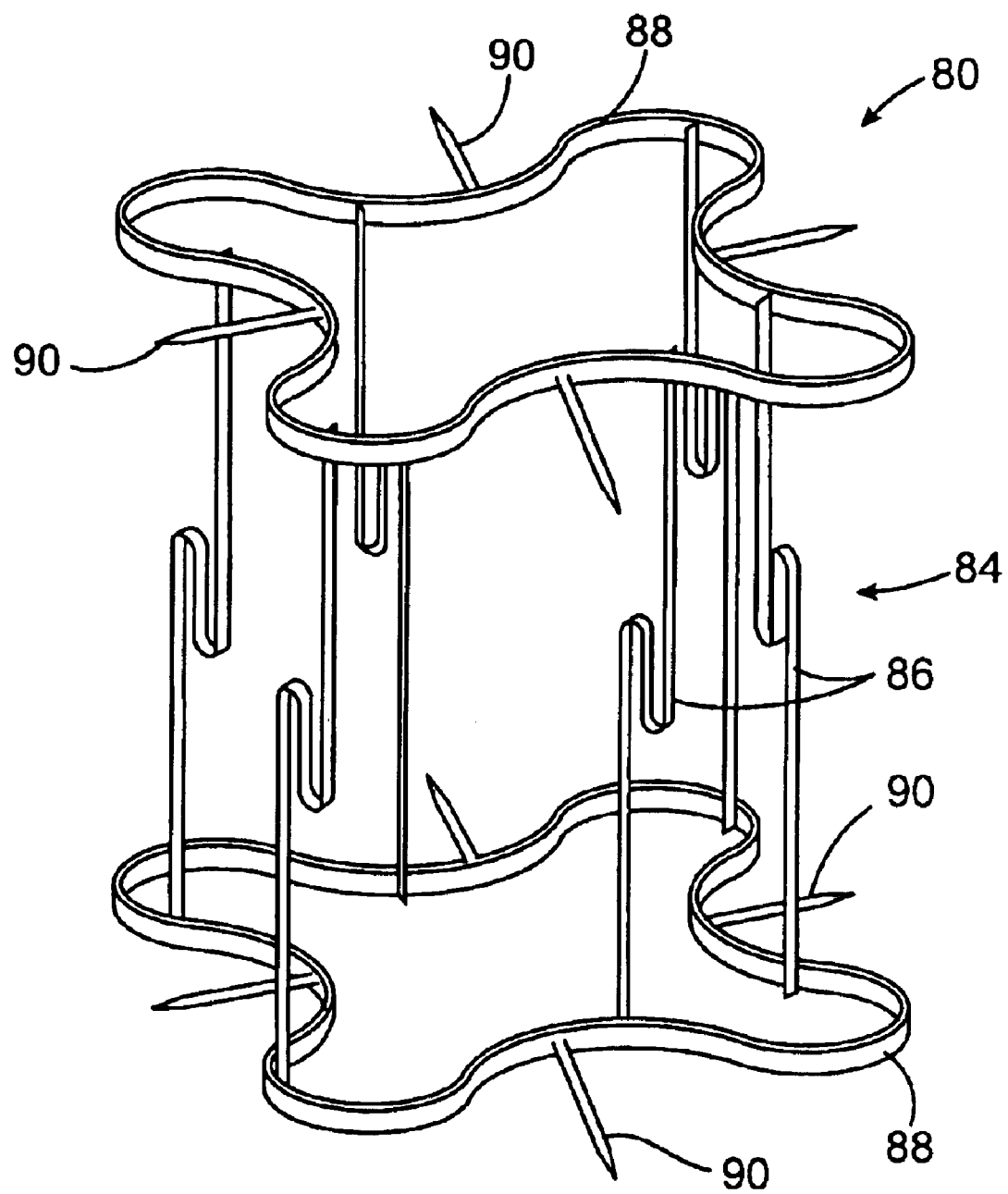
FIG. 11 is a perspective view of an alternative embodiment of an anastomosis device in a constrained configuration prior to use.
Figure 12:
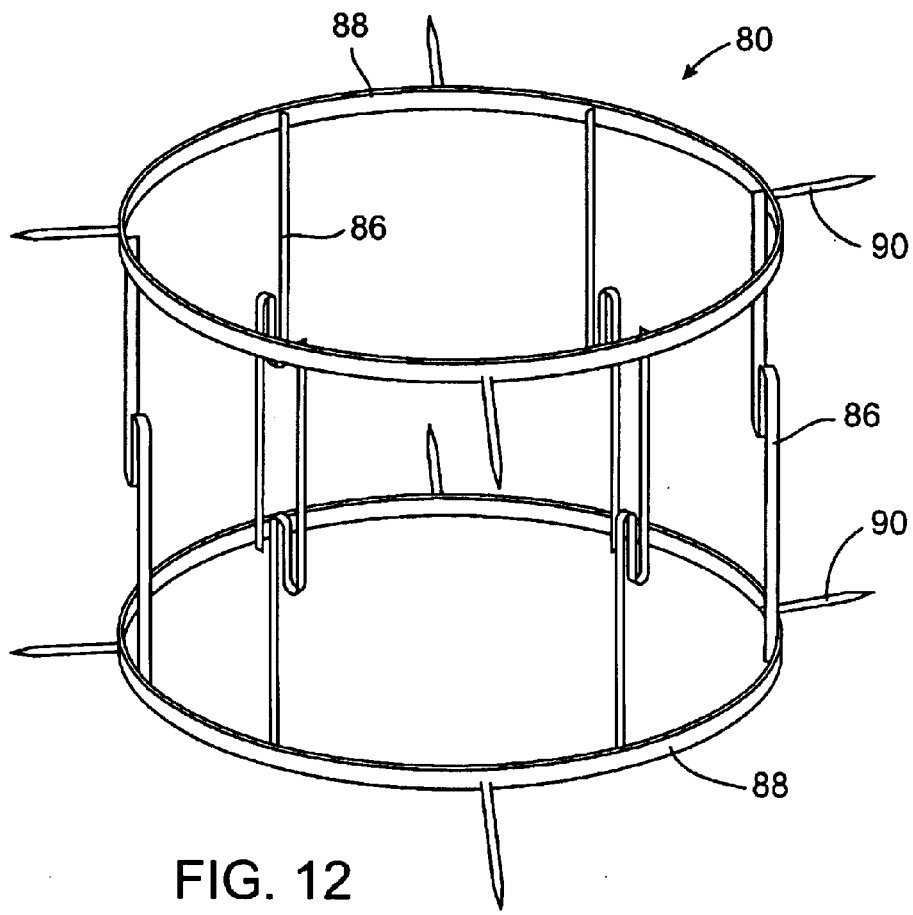
FIG. 12 is a perspective view of the anastomosis device of FIG. 11 in a deployed configuration.
Figure 13:
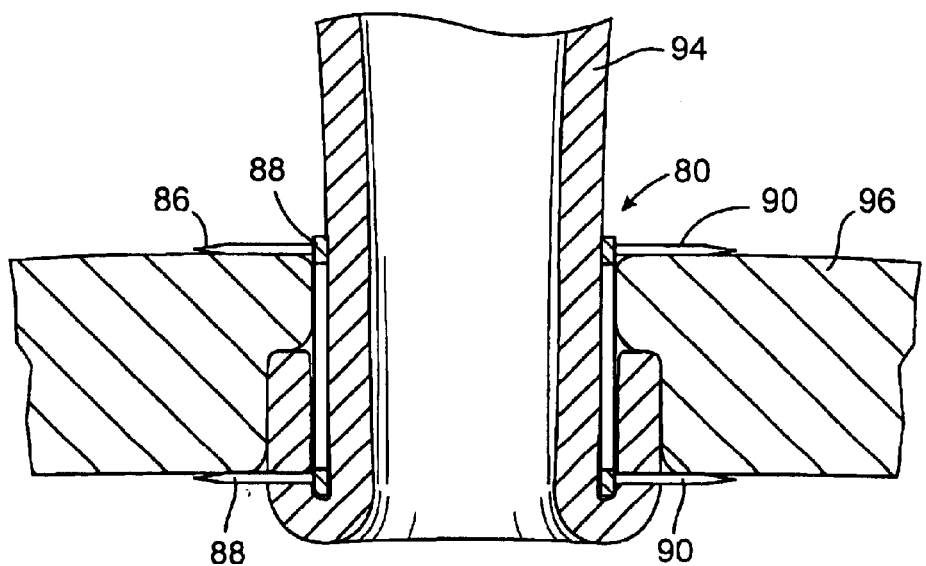
FIG. 13 is a side cross sectional view of the anastomosis device of FIG. 11 after deployment shown connecting a graft vessel to a target vessel.

FIGS. 11–13 illustrate an alternative embodiment of the superelastic or pseudoelastic anastomosis device 80 in a radially constrained configuration illustrated in FIG. 11 and in an expanded tissue retaining configuration illustrated in FIGS. 12 and 13. The anastomosis device 80 includes a device body 84 formed of a plurality of substantially parallel spring elements 86 interconnecting to end members 88. Extending from the end members 88 are a plurality of prongs 90 which in the expanded tissue supporting configuration illustrated in FIG. 13, form inner and outer flanges to trap the tissue of the target vessel 96. As in the previous embodiments, a graft vessel 94 is inserted through a center of the anastomosis device body 84 and is everted around the prongs 90 of at least one end the device body. The prongs 90 penetrate into or through the graft vessel tissue to retain the graft vessel on the anastomosis device.

The anastomosis device 80 with the graft vessel 94 everted around the anastomosis device is inserted in a radially constrained configuration illustrated in FIG. 11 into an opening in the target vessel 96. When the radially constraining member such as a retainer tube is removed from the anastomosis device 80, the anastomosis device spontaneously self deforms and returns to the configuration of FIG. 12 due to the superelastic or pseudoelastic properties of the material.

As shown in FIG. 13, a first set of the prongs 90 forms a flange at the inner wall of the target vessel. The spring elements 86 allow the distance between the end members 88 to adjust somewhat to target vessels 96 having walls of different thicknesses. The spring elements 86 may also apply a compression force to the wall of the target vessel 96 once the anastomosis device 80 has been deployed to provide improved sealing.

In an alternate embodiment of the anastomosis device 80 of FIGS. 11–13, the graft vessel 94 may be attached to the anastomosis device without everting. This may be done by providing axial prongs, hooks, or barbs on the inner rail member 88 and hooking an end of the graft vessel on the hooks, prongs, or barbs without everting.

Figure 14:
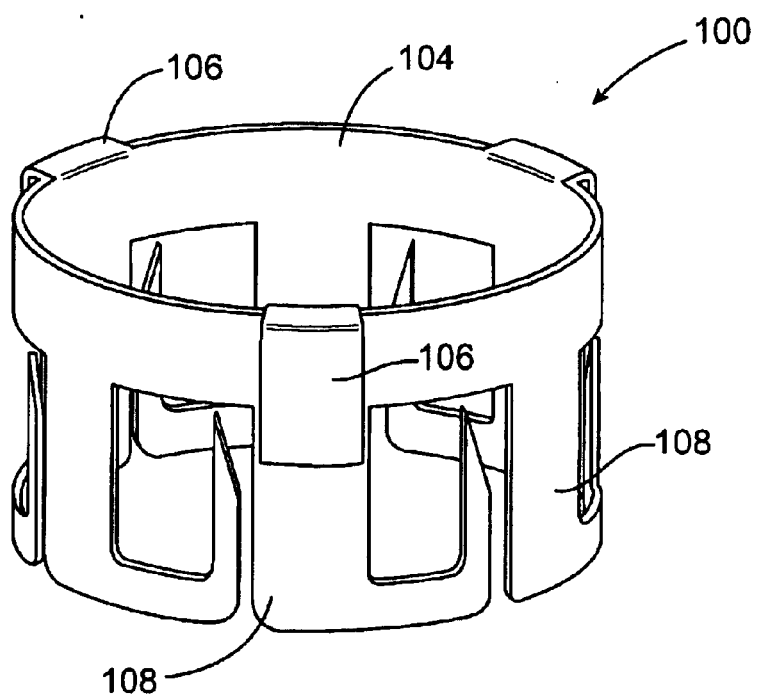
FIG. 14 is a perspective view of an alternative embodiment of an anastomosis device in a constrained configuration prior to use.
Figure 15:
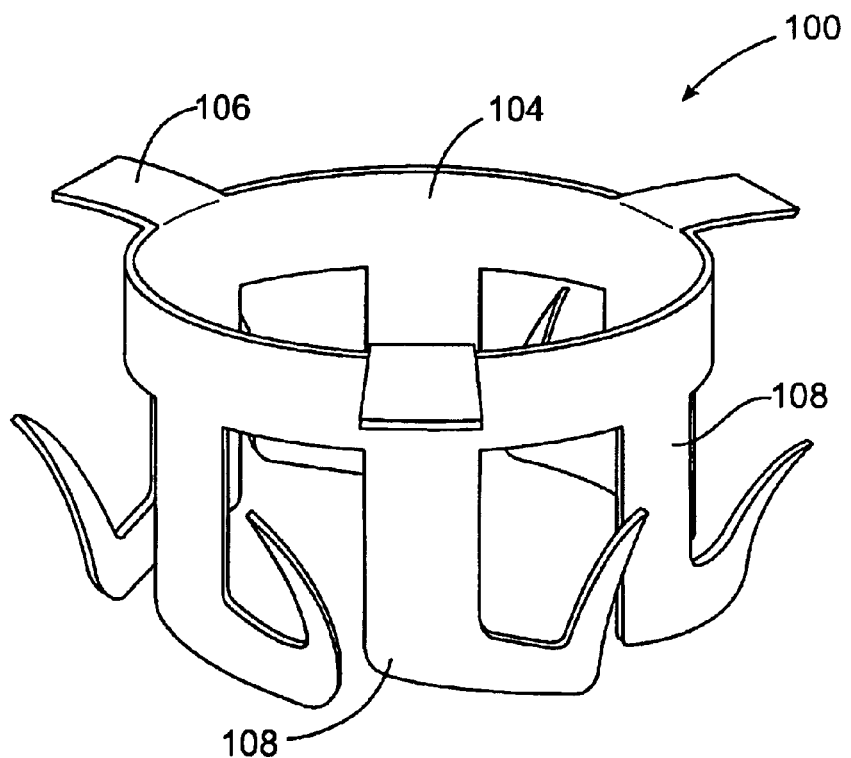
FIG. 15 is a perspective view of the anastomosis device of FIG. 14 in a deployed configuration.

An alternative embodiment of an anastomosis device 100 includes an anastomosis device body 104, legs 106, and hooks 108, as in the embodiment of FIGS. 1 and 2. The embodiment of FIGS. 14 and 15 differs from the embodiment of FIGS. 1 and 2 in that the legs 106 are folded outward and downward adjacent the body 104 in the radially constrained insertion configuration illustrated in FIG. 14. The legs 106 will spontaneously spring out to the flange forming configuration of FIG. 15 when the radially constraining member such as a retainer tube is removed for deployment of the anastomosis device 100.

Figure 16:
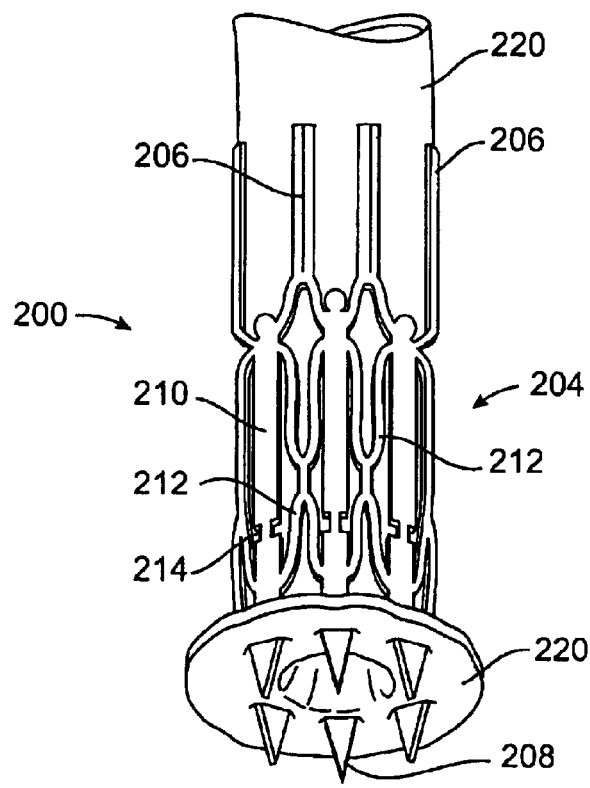
FIG. 16 is a perspective view of an alternative embodiment of an expandable body anastomosis device in a constrained configuration prior to use.
Figure 17:
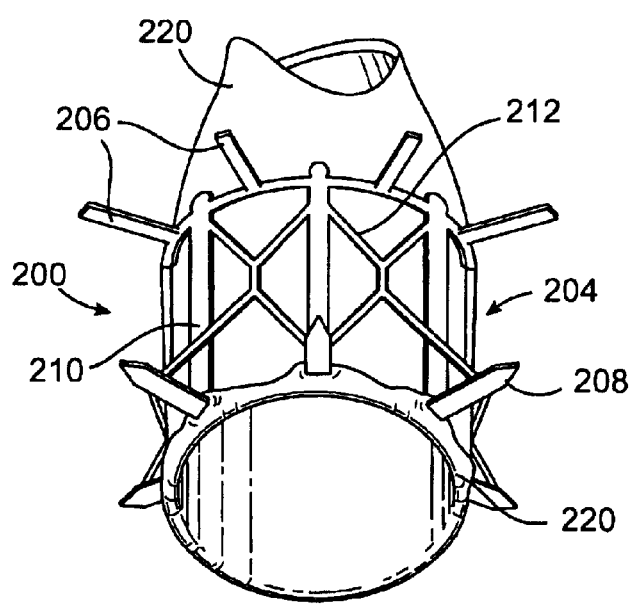
FIG. 17 is a perspective view of the anastomosis device of FIG. 16 in a deployed configuration.

FIGS. 16 and 17 illustrate an alternative embodiment of an anastomosis device 200 including a device body 204, legs 206 and pointed legs 208. The body 204 is formed of axially extending members 210 interconnected by struts 212 which allow the body to expand radially. Positioned between the body 204 and the pointed legs 208 are hinges 214. FIG. 16 illustrates the anastomosis device 200 in a radially constrained insertion configuration with a graft vessel 220 extending through an interior of the device body 204 and everted over the pointed legs 208. The pointed legs 208 penetrate and hold the everted end of the graft vessel 220 on the device 200.

For insertion, the anastomosis device 200 of FIG. 16 is radially constrained in a deployment tube (not shown). As the deployment tube is withdrawn from the device 200, the pointed legs 208 fold outward to form an inner flange, the device body 204 expands radially, and the legs 206 fold outward to form an outer flange. The radially expanding body 204 helps to stretch and support an opening in the target vessel.

Each of the anastomosis devices according to the present invention are preferably single piece devices which are formed in a substantially tubular shape. The anastomosis devices may be formed by laser cutting or punching from a tube or sheet of superelastic or pseudoelastic material. Alternatively, the devices may be formed from superelastic or pseudoelastic wire. The devices may be provided in varying sizes to join vessels of different sizes. The legs, hooks, prongs, and other device elements which have been discussed above with regard to the various embodiments may be used in varying numbers and arrangements depending on the particular application.

The invention has been described as an anastomosis device which is constrained for insertion in a radially constrained configuration with a deployment tool such as tube. However, the deployment tube may take other non-tubular shapes.

Although the invention has been primarily discussed with respect to coronary artery bypass surgery, the anastomosis devices of the present invention may by used in other types of anastomosis procedures. For example, the anastomosis device may be used in femoral-femoral bypass, vascular shunts, subclavian-carotid bypass, organ transplants, and the like. The devices according to the present invention may be used with venous grafts such as a harvested saphenous vein graft, arterial graft, such as a dissected mammal artery, or a synthetic prosthesis, as required.

Finally, the anastomosis devices according to the present invention have been illustrated as substantially cylindrical members. However, the devices can also be shaped into ovals, football shapes, or other shapes. Oval shapes can be particularly useful for accommodating small target vessels.

While the invention has been described in detail with reference to the preferred embodiments thereof, it will be apparent to one skilled in the art that various changes and modifications can be made and equivalents employed, without departing from the present invention.

What is claimed is:

1. A one-piece anastomosis device for connecting a graft vessel to a target vessel, comprising:
    a device body formed of a superelastic or pseudoelastic material, the body having an insertion configuration and a tissue holding configuration in which the body has an inner flange and an outer flange, the outer flange having a plurality of outer flange members and the inner flange having a plurality of inner flange members, wherein at least one of the outer flange members is substantially radially offset from at least one of the inner flange members in the tissue holding configuration; and wherein at least a portion of the body between the inner flange and the outer flange maintains a substantially constant diameter in both the insertion configuration and the tissue holding configuration.

2. The device of claim 1, wherein a portion of the device body between the inner flange and the outer flange is expandable from a first diameter in the insertion configuration to a second diameter in the tissue holding configuration.

3. The device of claim 1, wherein the superelastic or pseudoelastic material is a nickel titanium alloy.

4. The device of claim 1, wherein at least one of the inner flange elements is configured to penetrate and hold a graft vessel in place on the device body.

5. The device of claim 1, wherein the device body uses the superelastic or pseudoelastic properties of the material to self deform from the insertion configuration to the tissue holding configuration.

6. The device of claim 1, wherein at least one of the inner flange members is a hook.

7. The device of claim 1, wherein the outer flange members are configured to contact the outer wall of the target vessel without penetrating it.

8. The device of claim 1, wherein at least one of the inner and outer flanges is radially constrained in the insertion configuration for insertion into the target vessel and when released self deforms to the tissue holding configuration.

9. A tube deployed anastomosis system for connecting a graft vessel to a target vessel, comprising:
    a deployment tube; and
    an anastomosis device formed of a superelastic or pseudoelastic material, the device having an insertion configuration and a tissue holding configuration in which the device has an inner flange and an outer flange, the outer flange having a plurality of outer flange members and the inner flange having a plurality of inner flange members, wherein at least one of the outer flange members is substantially radially offset from at least one of the inner flange members in the tissue holding configuration, and wherein at least a portion of the body between the inner flange and the outer flange maintains a substantially constant diameter in both the insertion configuration and the tissue holding configuration;
    wherein at least one of the inner and outer flanges is radially constrained in the deployment tube in the insertion configuration for insertion into the target vessel and when released from the deployment tube self deforms to the tissue holding configuration.

10. The device of claim 9, wherein a portion of the device body between the inner flange and the outer flange is expandable from a first diameter in the insertion configuration to a second diameter in the tissue holding configuration.

11. The device of claim 9, wherein the superelastic or pseudoelastic material is a nickel titanium alloy.

12. The device of claim 9, further comprising a plurality of tissue penetrating elements for penetrating and holding a graft vessel in place on the device body.

13. The device of claim 12, wherein the tissue penetrating elements extend radially outwardly from the device body for holding an everted end of the graft vessel.

14. The device of claim 9, wherein the device body uses the superelastic or pseudoelastic properties of the material to self deform from the insertion configuration to the tissue holding configuration.

15. A method of deploying an anastomosis system for connecting a graft vessel to a target vessel, the method comprising:
    providing an anastomosis device deployable to form an inner flange having a plurality of inner flange members and an outer flange having a plurality of outer flange members;
    penetrating and holding the graft vessel with at least one of the inner flange members; and
    deploying the one piece device by self deformation to a tissue holding configuration in which the device has an inner flange and an outer flange and traps the target vessel tissue between the inner flange and the outer flange, wherein at least one of the outer flange members is substantially radially offset from at least one of the inner flange members, and wherein at least a portion of the device between the inner flange and the outer flange maintains a substantially constant diameter before and after the deploying.

16. The method of claim 15, wherein the one piece device is deployed by removing a radially constraining deployment tool from the device.

17. The method of claim 16, wherein the deployment tool is a deployment tube which receives the tubular device, and wherein the deployment tube is inserted partially into the target vessel wall and then withdrawn to deploy the one piece device from the deployment tube.

18. The method of claim 15, wherein the one-piece device is deployed by employing the superelastic or pseudoelastic property of a material from which the one-piece device is formed.

19. The method of claim 15, wherein the graft vessel is everted around the one piece device.

20. The method of claim 15, wherein the deployed one piece device abuts an intima of the graft vessel against an intima of the target vessel.

21. A one-piece anastomosis device for connecting a graft vessel to a target vessel, comprising:

a device body formed of a shape memory material, the body having an insertion configuration and a tissue holding configuration in which the body has an inner flange and an outer flange, the outer flange having a plurality of outer flange members and the inner flange having a plurality of inner flange members, wherein at least one of the two sets of flange members does not penetrate tissue; and wherein at least a portion of the body between the inner flange and the outer flange maintains a substantially constant diameter in both the insertion configuration and the tissue holding configuration.

22. The one-piece anastomosis device of claim 21, wherein at least one of the two sets of flange members has blunt ends.

23. The one-piece anastomosis device of claim 21, wherein the outer flange members do not penetrate tissue.

24. The one-piece anastomosis device of claim 21, wherein at least a portion of the body is an uninterrupted ring.

* * * * *